United States Patent
Mills et al.

(10) Patent No.: US 11,589,949 B1
(45) Date of Patent: Feb. 28, 2023

(54) SYSTEM AND METHODS OF CREATING A 3D MEDICAL REPRESENTATION FOR USE IN PERFORMING RECONSTRUCTIVE SURGERIES

(71) Applicants: Jordan Mills, New York, NY (US); Matthew Zartman, New York, NY (US)

(72) Inventors: Jordan Mills, New York, NY (US); Matthew Zartman, New York, NY (US)

(73) Assignee: MirrorMe3D, LLC, New York, NY (US)

( * ) Notice: Subject to any disclaimer, the term of this patent is extended or adjusted under 35 U.S.C. 154(b) by 395 days.

(21) Appl. No.: 16/376,783

(22) Filed: Apr. 5, 2019

Related U.S. Application Data

(60) Provisional application No. 62/653,177, filed on Apr. 5, 2018, provisional application No. 62/653,159, filed on Apr. 5, 2018.

(51) Int. Cl.
    *A61B 90/00* (2016.01)
    *A61B 5/00* (2006.01)
    (Continued)

(52) U.S. Cl.
    CPC ............ *A61B 90/37* (2016.02); *A61B 5/0064* (2013.01); *A61B 34/20* (2016.02); *A61B 90/361* (2016.02);
    (Continued)

(58) Field of Classification Search
    CPC ....... A61B 90/37; A61B 5/0064; A61B 34/20; A61B 90/361; A61B 6/032; A61B 5/0077; A61B 34/10
    See application file for complete search history.

(56) References Cited

U.S. PATENT DOCUMENTS

| | | | |
|---|---|---|---|
| 8,706,672 B2 * | 4/2014 | Malfliet | G06T 7/0012 706/47 |
| 10,758,321 B2 * | 9/2020 | Stone-Collonge | A61C 7/08 |

(Continued)

FOREIGN PATENT DOCUMENTS

| | | | |
|---|---|---|---|
| EP | 1027681 A1 * | 8/2000 | G06T 7/80 |
| EP | 1027681 A4 * | 9/2001 | A61C 9/0046 |
| WO | WO-2017175055 A1 * | 10/2017 | A61B 5/0062 |

OTHER PUBLICATIONS

Xia J, Wang D, Samman N, Yeung RW, Tideman H. Computer-assisted three-dimensional surgical planning and simulation: 3D color facial model generation. Int J Oral Maxillofac Surg. Feb. 2000;29(1):2-10. PMID: 10691135. (Year: 2000).*

(Continued)

*Primary Examiner* — Boniface Ngathi N
*Assistant Examiner* — Zainab Mohammed Aldarraji
(74) *Attorney, Agent, or Firm* — Stroock & Stroock & Lavan LLP

(57) ABSTRACT

A computer specific system for receiving a plurality of medical imaging specific 3D patient specific data sets from different 3D data sources, for a patient receiving reconstructive surgery, locating and applying a plurality of landmarks to each data set, and performing an overlay analysis procedure that aligns the 3D data sets from the different 3D data sources to create a 3D medical image representation of the patient's tissue. The 3D representation can be used to create 3D models for use by surgeons to perform reconstructive surgical procedures.

12 Claims, 8 Drawing Sheets

(51) Int. Cl.
    *A61B 34/20*     (2016.01)
    *A61B 6/03*     (2006.01)
    *A61B 34/10*     (2016.01)

(52) U.S. Cl.
    CPC ............ *A61B 5/0077* (2013.01); *A61B 6/032* (2013.01); *A61B 34/10* (2016.02)

(56) References Cited

U.S. PATENT DOCUMENTS

| | | | | |
|---|---|---|---|---|
| 2012/0010533 A1* | 1/2012 | Arnett | ................ | G06K 9/00281 600/590 |
| 2013/0249907 A1* | 9/2013 | Humphries | ........... | G06T 7/0012 345/420 |
| 2016/0247017 A1* | 8/2016 | Sareen | .................... | G06T 19/00 |
| 2017/0200272 A1* | 7/2017 | Buisseret | ................ | G06T 7/149 |
| 2017/0258526 A1* | 9/2017 | Lang | .................... | A61B 17/155 |

OTHER PUBLICATIONS

Dr. M. Mohamed Sathik et al., Ray Casting for 3D Rendering—A Review, International Journal of Innovations in Engineering and Technology (IJIET), vol. 5 Issue 1, Feb. 1, 2015.

\* cited by examiner

US 11,589,949 B1

SYSTEM AND METHODS OF CREATING A 3D MEDICAL REPRESENTATION FOR USE IN PERFORMING RECONSTRUCTIVE SURGERIES

CROSS-REFERENCE TO RELATED APPLICATIONS

This application claims the benefit of U.S. Provisional Application No. 62/653,159 and U.S. Provisional Application No. 62/653,177, both of which were filed on Apr. 5, 2018 and are incorporated by reference herein in their entirety.

BACKGROUND

For aesthetic and reconstructive surgeries, medical personnel currently rely on medical imaging that is disjointed, requires manual manipulation, and lacks sufficient details.

SUMMARY

Various embodiments of the present invention provide systems and methods for surgeons to utilize medical imaging in a manner which provides a comprehensive view of the patient's current and intended conditions, and increases the accuracy and efficiency of the surgeon during the entire surgical procedure (pre-operation, intra-operation, and post-operation).

In some embodiments, the systems and methods may include live collaboration on the most current patient data available among treating physicians and surgeons to be utilized during pre-operative planning, intra-operative execution, and post-operative analysis.

In some embodiments, the invention provides a computer-implemented method of processing medical imaging data for aesthetic and reconstructive surgeries, comprising: receiving medical imaging data for a patient undergoing an aesthetic or reconstructive surgery, wherein the medical imaging data comprises a plurality of patient-specific 3D digital data sets from different 3D data sources; performing a landmark identification procedure, locating and applying a plurality of predetermined landmarks to each digital data set; and performing an overlay analysis procedure, aligning the digital data sets from the different sources.

In some embodiments, the medical imaging data further comprises one or more patient-specific 2D digital data sets.

In some embodiments, the method further comprises transforming the landmarks from the 2D digital data sets to 3D space.

In some embodiments, the transforming is performed using raycasting.

In some embodiments, the plurality of predetermined landmarks comprise at least five landmarks representing the right eye, left eye, nose right mouth tip, and left mouth tip.

In some embodiments, the aligning is based on orbit and eye structure.

In some embodiments, the method further comprises creating at least one of a baseline model, a simulated model, a template, and a guide based on the processed medical imaging data.

In some embodiments, the creating is performed using color-jet 3D printing, selective laser sintering printing, or stereolithography printing.

In some embodiments, the method further comprises providing one or more digital displays, comprising at least one of: a surgical planning display for pre-operative use, comprising a 3D display of the medical imaging data, the processed medical imaging data, or a simulated model based on the processed medical imaging data; a live data feed for intra-operative use, including an active data intake device updating in real time; and an automated data comparison display for post-operative use, configured to compare pre-operative and post-operative conditions.

In some embodiments, the active data intake device comprises an infrared scanner or depth sensing technology.

In some embodiments, at least one digital display comprises a virtual reality, augmented reality, or mixed reality device.

In some embodiments, the invention provides a patient-specific 3D model for aesthetic and reconstructive surgeries, produced by: receiving medical imaging data for a patient undergoing an aesthetic or reconstructive surgery, wherein the medical imaging data comprises a plurality of patient-specific 3D digital data sets from different 3D data sources; processing the medical imaging data by: performing a landmark identification procedure, locating and applying a plurality of predetermined landmarks to each digital data set; and performing an overlay analysis procedure, aligning the digital data sets from the different sources; and creating the 3D model based on the processed medical imaging data.

In some embodiments, the medical imaging data further comprises one or more patient-specific 2D digital data sets.

In some embodiments, the model is created using additive manufacturing technology.

In some embodiments, the model is created using color-jet 3D printing, selective laser sintering printing, or stereolithography printing.

In some embodiments, the model comprises at least one of a baseline model, a simulated model, a template, and a guide.

Additional features and advantages of the present invention are described further below. This summary section is meant merely to illustrate certain features of the invention, and is not meant to limit the scope of the invention in any way. The failure to discuss a specific feature or embodiment of the invention, or the inclusion of one or more features in this summary section, should not be construed to limit the invention as claimed.

BRIEF DESCRIPTION OF THE DRAWINGS

The foregoing summary, as well as the following detailed description of certain embodiments of the application, will be better understood when read in conjunction with the appended drawings. For the purposes of illustrating the systems and methods of the present application, there are shown in the drawings preferred embodiments. It should be understood, however, that the application is not limited to the precise arrangements and instrumentalities shown. In the drawings.

DETAILED DESCRIPTION

Figure 1:
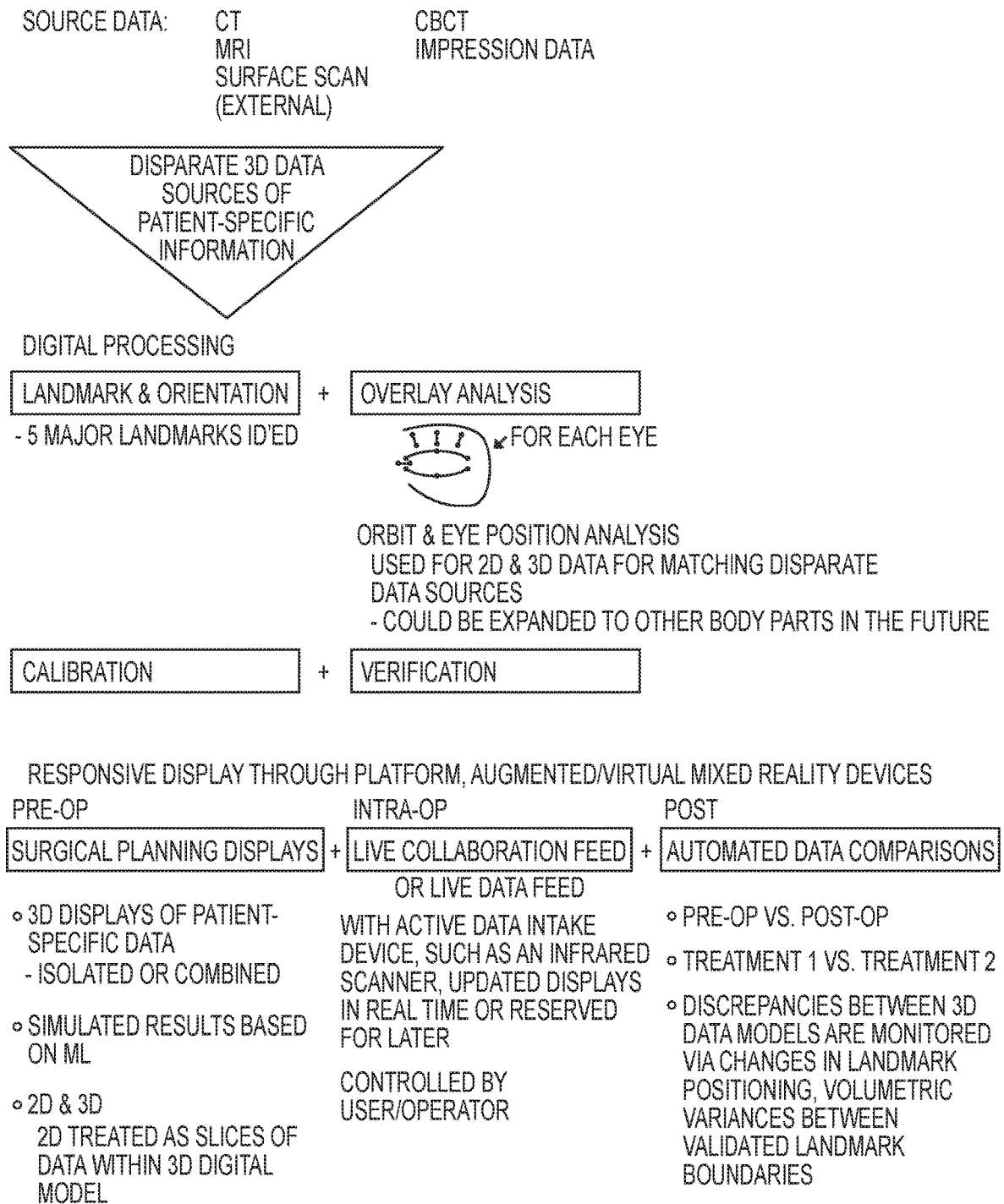
FIG. 1 is a schematic illustrating source data, digital processing, and displays, according to some embodiments of the invention.

For reconstructive surgical procedures such as breast, face, head and neck, and oral cavity surgeries, surgeons and other physicians and medical personnel currently rely on an assortment of medical imaging to assess the patient's current condition, to diagnose as to plan for treatment, and to execute during the surgical procedure. The medical imaging is currently disjointed, requires manual manipulation for study, and lacks sufficient details observable through three-dimensional displays of simultaneous data points.

In addition, surgical plans and treatments requiring more than one surgeon or physician have no central point of access for all collaborating surgeons to view, analyze, annotate, and/or discuss patient data. Typically, surgeons rely on USB technology or CDs to share patient data, which often means using outdated patient data and relying on handwritten notes during pre-operative planning with other surgeons and physicians assigned to the case and for intra-operative reference and guidance.

Embodiments of the present invention provide methods and systems for surgeons to utilize medical imaging in a manner which provides a comprehensive view of the patient's current and intended conditions, and increases the accuracy and efficiency of the surgeon during the entire surgical procedure (pre-operation, intra-operation, and post-operation).

Embodiments of the present invention also provide methods and systems for collaboration among surgeons/physicians and/or other medical personnel, which can reduce or eliminate the need for USB technology, manual file sharing (e.g., via software such as Dropbox), CDs, and/or paper files, among others.

The methods and systems described herein have applications for various anatomies, for example, for reconstructive surgical procedures involving external and/or internal soft tissue such as face, head and neck, breast, and oral cavity. As used herein, "Reconstructive Surgeons" using the disclosed technology may be plastic surgeons (both cosmetic/aesthetic and reconstructive), oral surgeons, otolaryngologists, dentists, prosthodontists, ophthalmologists, dermatologists, or other specialists treating cases within this field of use (e.g., craniofacial surgeons, craniomaxillofacial surgeons, oculoplastic surgeons and orthopedic surgeons).

In some embodiments, the invention provides methods and systems by which all currently available 3D medical imaging (imaging data including, but not limited to, CT scans, MRI scans, ultrasound scans, 3D soft tissue scans, 3D stereophotogrammetric images, and 3D laser scans) is processed using new computer-implemented processes to auto assign landmarks on the imaging data for: pre-operative planning, guidance and analysis; intra-operative reference, guidance and analysis; and/or post-operative analysis and results assessment.

In some embodiments, the invention provides methods and systems by which all 2D photography and 3D medical imaging is combined intuitively using new computer-implemented processes and displayed for: pre-operative planning, guidance and analysis; intra-operative reference, guidance and analysis; and/or post-operative analysis and results assessment.

To date, surgeons must manually combine imaging data for surgical planning and rely on antiquated methods for analysis and display during the consultation/diagnosis stage, the surgical procedure stage, and the post-operative stage of the surgical process.

With the systems and methods of embodiments of the present invention, surgeons and medical personnel can combine imaging data more accurately and can create surgical plans based on a more complete understanding of the patient's condition(s).

Using systems and methods according to embodiments of the present invention, surgeons can: analyze patient data at any stage within the surgical process; survey and document the patient's condition(s) during the surgical process; reference prior condition(s) or anticipated/simulated post-operative condition(s); view medical imaging during any phase of the surgical process via a smartphone, tablet, or other screens containing augmented and/or virtual reality mechanisms; annotate areas of importance with detailed notes for later reference; collaborate in real time with other physicians and surgeons (medical personnel) using the same patient data necessary for successful planning and execution; and/or archive and reference patient data for a comprehensive understanding of the patient's full treatment history.

Embodiments of the present invention overcome the shortcomings of previous display and analysis mechanisms such as: displays of 2D photos printed and adhered to a wall; 2D displays of stereophotogrammetric camera photos via a computer or television screen; hand drawing and sketching using visual estimation ("eye-balling"); and 2D displays of manual manipulation using off-the-shelf 3D modeling software.

In some embodiments, the invention provides a method including the steps of: (1) processing 3D stereophotogrammetric and/or 3D laser scanning output data to create virtual models that can be used by a surgeon for pre-operative planning and/or intra-operative planning; (2) analyzing and annotating the virtual model(s); and (3) displaying, viewing, and interacting with the virtual model(s) including assigned annotations and analysis during the surgical process with the assistance of mixed reality technology and/or other virtual or augmented reality mechanisms, in addition to traditional smartphones, tablets, screens and monitors.

In some embodiments, the 3D data may include pre-operative (baseline) data, simulated post-operative data, as well as other medical imaging. In some embodiments, the virtual models can also contain pre-operative and post-operative data of the external soft tissue. Further, in some embodiments, additional 3D data obtained at any point during the surgical process can be combined with the virtual models to give the surgeon the most comprehensive data set for surgical planning including planning before, during, or after the surgery.

Embodiments of the present invention can use 3D data sourced from multiple apparatus including, but not limited to, 3D stereophotogrammetric cameras, 3D laser scanning, 3D surface scanning, and 3D photography, among many others.

In some embodiments, the step of processing the 3D data includes the step of ingesting the output data from the source apparatus and displaying and viewing the data for surgical planning. Further, this step can include digital manipulations of the output data under the supervision of the attending surgeon for the patient. In some embodiments, using data quality checkpoints between pivotal landmarks on the facial soft tissue, all digital manipulations may be screened for accuracy of the simulation and may require approval from the surgeon before acceptance into the system.

Additionally, embodiments of the present invention can be used for processing the images so that surgeons can use the 3D data for analysis and planning. This includes displaying and viewing the 3D data on smartphones, tablets, screens, and monitors. Further, the 3D data can be experienced through mixed reality, augmented reality, and virtual reality mechanisms.

Using computer-implemented landmarking processes (e.g., as detailed further below), the 3D data can be oriented to match the current orientation of the patient during a procedure and/or can be adjusted by the surgeon for the best view necessary for interpretation or review.

In some embodiments, the invention provides a method comprising: digital processing of 3D data for creating a virtual model for viewing and display; digital processing of 3D data for creating a virtual baseline model to be used for digital manipulation to obtain a simulated model; analyzing the 3D data; communicating digitally with other medical professionals within a same or different field of use; and/or digital processing of 3D data for generating 3D printed guides, templates, mold, splints and/or other apparatuses for the use by a surgeon during pre-operative planning, during the procedure, and for post-operative assessment.

Embodiments of the present invention may include computer-executable instructions stored on a non-transitory computer-readable medium for viewing, displaying, and digital manipulation of 3D data, including, but not limited to, analysis and annotation by means of smartphones, tablets, screens, and monitors. This also includes viewing, displaying, and digital manipulation through virtual, mixed, and augmented reality mechanisms. The computer-implemented methods can be controlled by the surgeons through the smartphones, tablets, screens, and monitors as well as devices with voice activation capabilities, and motion sensing technology employed by wearable devices and optical sensing systems.

In some embodiments, an illustrative flow may be generally as follows: (1) the surgeon or staff member takes a 3D scan or 3D photo of the normative anatomy; (2) the surgeon or staff member can then prescribe any changes to the anatomical form to produce a simulated model (alternatively, the normative anatomy can be used if the shape is to be the same post-operatively); (3) software according to embodiments of the present invention converts the scan/photo into a mesh which can be manipulated by 3D modeling software; (4) using extracted dimensions obtained by the scan/photo, the software uses the digital file to create a guide, template, mold, and/or splint as well as 3D models of the baseline and/or simulated anatomy of the patient being treated; and (5) the models, guides, templates, etc. thus created are 3D printed for the surgeon. In some embodiments, the systems and methods of the present invention may provide surgeons the capability of 3D printing in house through packaged files generated by software for the purpose of such 3D printing.

Figure 2:
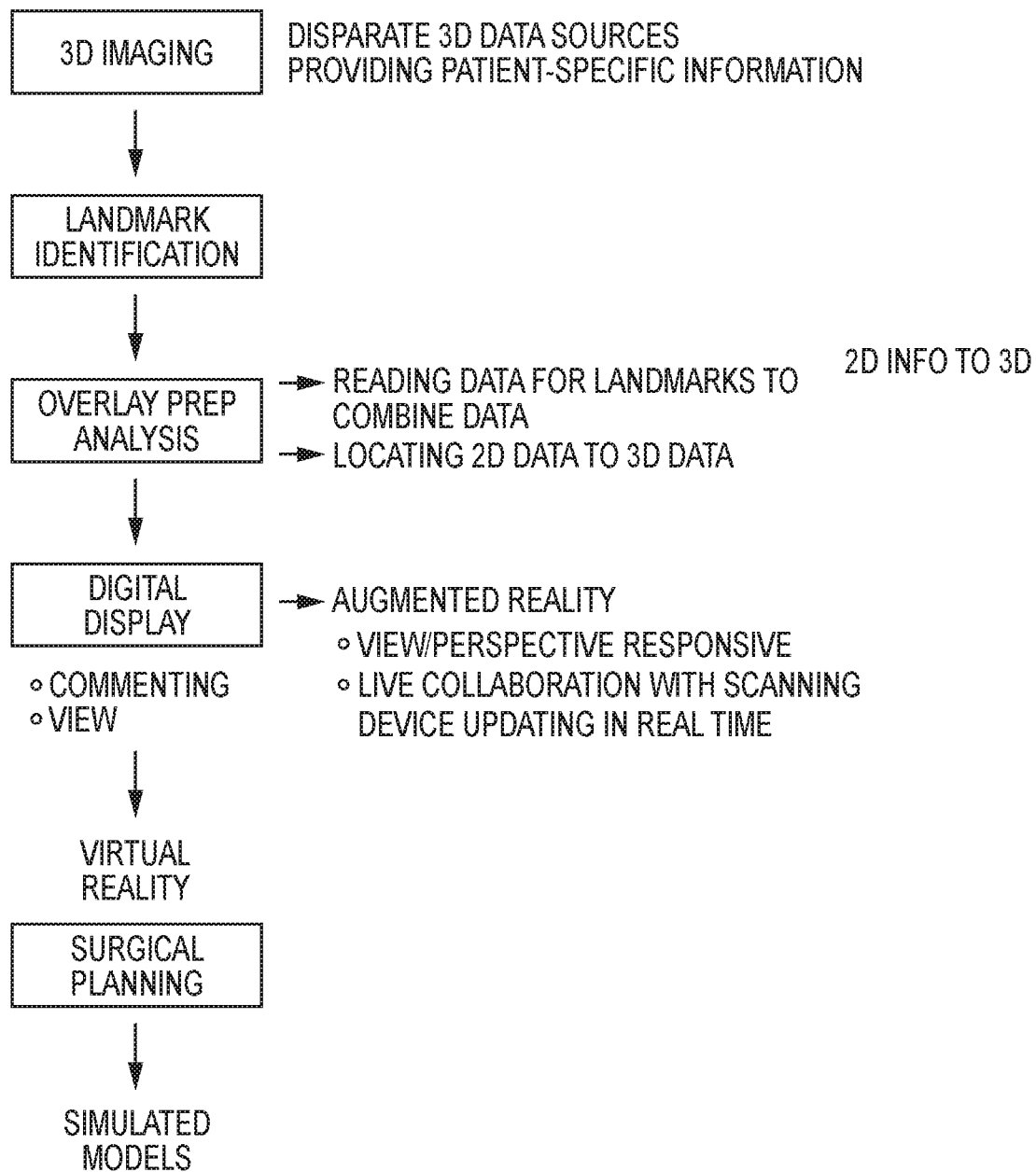
FIG. 2 is a flowchart of an illustrative method, according to some embodiments.

FIG. 1 is a schematic illustrating source data, digital processing, and displays according to some embodiments of the invention, as detailed further below. FIG. 2 is a flowchart of an illustrative method, according to some embodiments.

Source Data

Source data (e.g., facial anatomical data) can exist in both 2D and 3D data sets. Source data is currently produced by hardware or machines that require manufacturer-specific software for viewing the data or require using digital viewers that do not match disparate data sets (i.e., data produced from different hardware or machines). Embodiments of the present invention can overcome these problems by applying a digital data ingestion process that: (1) uniquely identifies the data set as 2D or 3D; (2) applies landmarks accordingly; and (3) calibrates and verifies newly attributed landmarks.

Landmarking and Orientation

When a data set is identified as 2D, software according to embodiments of the present invention can apply landmarks to different points on the face which are determined to be most reliable for maintaining accuracy. For example, in some embodiments, the software uses the exact point where the upper eye lid and lower eye lid converge, and not merely the zone identified as the medial canthi. This produces greater accuracy when building comparative datasets. The software then auto-labels that 2D data source (most often a 2D photograph) as a "slice" which then can be used alongside 3D data presenting a similar view of the patient.

When a data set is identified as 3D, software according to embodiments of the present invention can apply landmarks according to one or more of the following steps:

Vantage Point Centrality

In some embodiments, vantage point centrality may be established by the process described below, using: a number of points on a sphere, approximately uniformly distributed; a metric (such as distance) to determine whether to label two points on the sphere as "neighbors"; and a map of points to "truth values" indicating which of the points on the sphere are in consideration (e.g., a list of points from which faces were detected).

1. Using the metric for judging neighbors, create a graph with a vertex for each point in the set and an edge between two vertices if those two points are neighbors. In some embodiments, the metric may be selected to minimize the variance of the number of neighbors of each vertex, so that on whole most vertices have close to the same number of neighbors.

2. Assign a measure of "closeness centrality" to each vertex. The closeness centrality is defined as $C=1/d(x, y)$, where $d(x, y)$ is the shortest path distance between any two vertices x and y, and this denominator is summed over all pairs of connected vertices on the graph.

3. After assigning a closeness centrality measure to each vertex, select the vertex with the highest value, and this the best vantage point.

Finding the Roll

Now that we have found the best vantage point, we can assume that we are looking at the model head on. However, that does not account for rotation about the Z axis, called "roll". We still might be looking at the model upside down, or sideways. In order to figure out this rotation, we use a landmarking tool to determine which rotation yields the most reasonable landmarks. To determine what is most reasonable, we use the fact that landmarks are guessed to be in relatively stable, predictable places when the face is at a normal roll, but are somewhat randomly distributed when the face's orientation is very wrong. We start by taking a snapshot of the model rotated about the Z axis (where Z is the direction the camera is looking), for each degree of a full rotation, yielding 360 images which are rotations of the original. For each of these images we then: (1) run a landmarking prediction provided by a trained neural net; and (2) record these landmarks in a table mapping the rotation used to generate the image to a list of the landmarks, for each of the 360 images. Next, we find the optimal rotation (e.g., as described below).

Landmark Clustering

In some embodiments, landmark clustering may be performed by the process described below, using a map M of rotations to point sets, where the point sets represent landmark sets in 2D space.

1. For each rotation X, transform the landmarks stored in M[X] by a rotation of −X. For example, if rotation 180 had the first landmark in the top left of the image, then a rotation of −180 would put the landmark in the bottom right of the image. The purpose of this is to put all the landmarks in the frame of reference of the original landmark set. Do this for each rotation, yielding a list of transformed point sets, where each point set contains five transformed landmarks.

2. This transformed list will be our list of guesses. Next, find the average distance between each right eye guess and each left eye guess. This distance is referred to herein as the interocular distance, or IOD.

3. Two guesses may be considered "neighbors", for example, if the distance between the right eyes is less than 10% of the average IOD, and the distance between the left eyes is less than 10% of the average IOD. For each rotation, calculate how many neighbors that guess has and record those neighbor counts in a list.

4. Run the neighbor count list through a gaussian filter to smooth it out and remove some noise.

5. Find the maximum value of the neighbor count list (or, if the maximum appears in several places, the middle point of the largest continuous set of maximum values). The rotation that corresponds to the maximum value on this neighbor count list is considered the optimal rotation, because it represents the center of the largest cluster of landmarks, and clusters of landmarks represent more accuracy through consistency.

6. Return this rotation, or roll.

Locating Landmarks in 3D

Now that we have the optimal roll, we can rotate our model about the Z axis by this rotation. Finally, we are looking at our face model in the proper orientation. The last step is to go from landmarks on our 2D image to points in 3D that represent the landmarks on the 3D model. This can be done using a process called raycasting, a process that is known in the art and is described in a 2015 article, entitled "Ray Casting for 3D Rendering—A Review," published in the International Journal of Innovations in Engineering and Technology (IJIET). For example, in some embodiments, Open GL can be used to turn the points into a ray that hits the points in the 2D plane and goes forward in the 2D plane and goes forward in the camera's Z direction. With that ray in 3D space, we raycast to the object by iterating through each face in the object's mesh and determining whether our ray intersects that face. If we end up with multiple faces on the object mesh that the ray intersected with, we choose the face closest to the camera. Each face is composed of three vertices, so to choose one single point we pick the point which is closest to the intersection point of the ray and the face. Thus, we have a vertex that approximately represents where the ray intersects with the object. The vertex is our landmark point in 3D space. We repeat this process for each of the five landmarks. We now have five landmark points, in 3D space that represent the right eye, left eye, nose, right mouth tip, and left mouth tip on the face.

Overlay Analysis

Once 3D data has been ingested and assigned landmarks, an overlay analysis process may be applied to automate alignment of data from different hardware/machine sources and data depicting different information (e.g., CT is bony data, sometimes muscle is included; MRI is detailed muscle; CBCT is bony data, typically just of the oral cavity; surface scan or external scan is a 3D photo/scan of the face) based on the newly generated landmarks from the ingestion process. For this, the orbit and eye structure is preferably used as the basis for understanding the relationship between the data sets.

Case Examples

Figure 3:
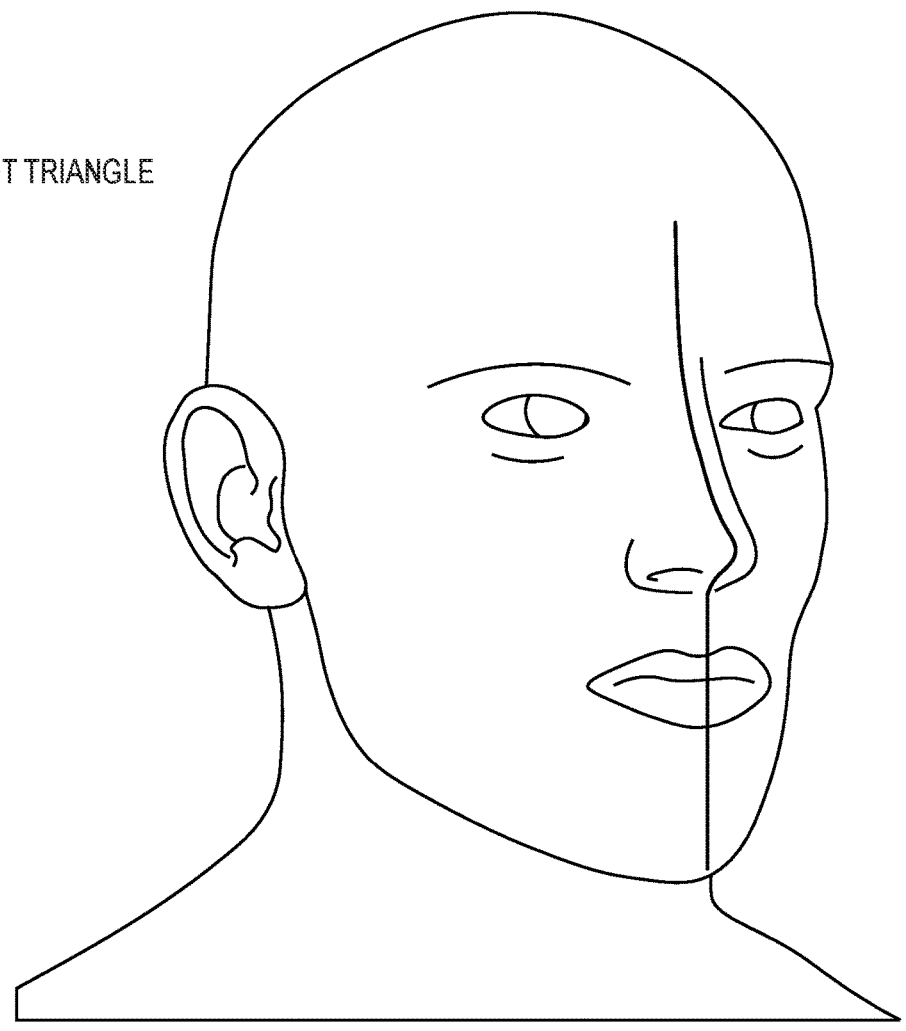
FIGS. 3-5 show various views of measurements and analysis of a patient undergoing rhinoplasty, according to some embodiments.
Figure 3:
Figure 4:
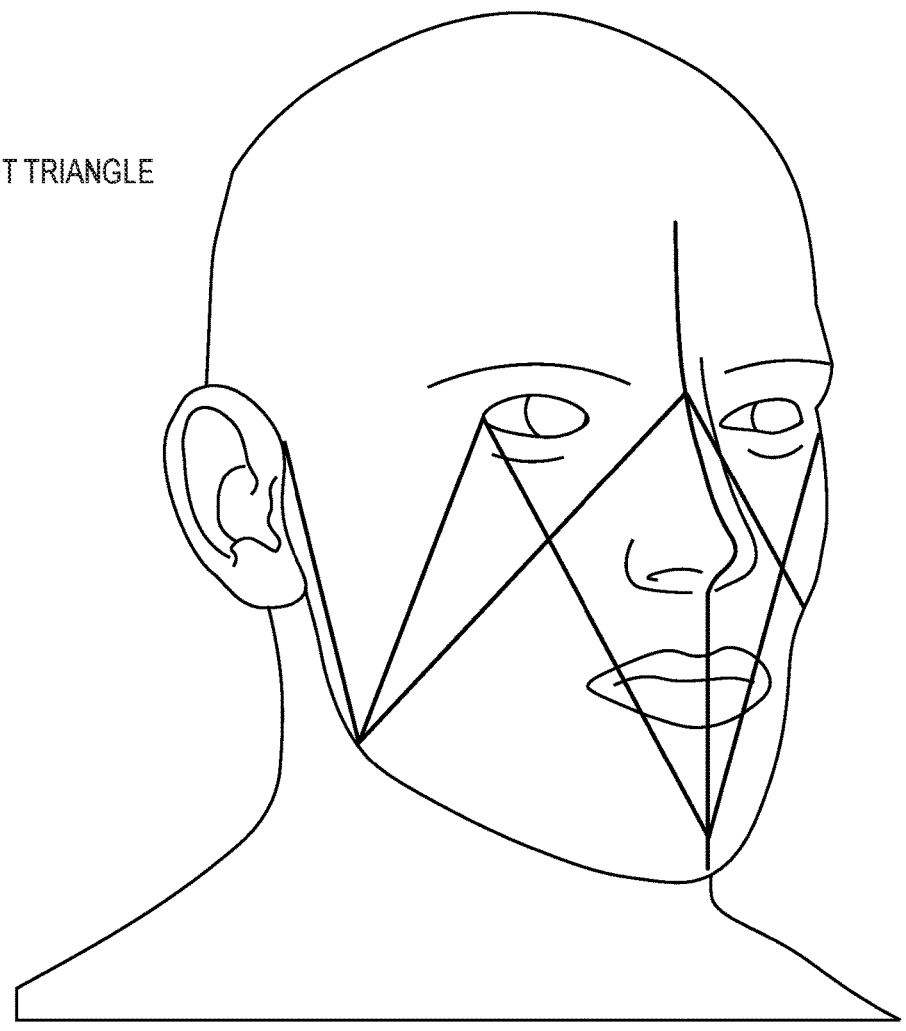
Figure 5:
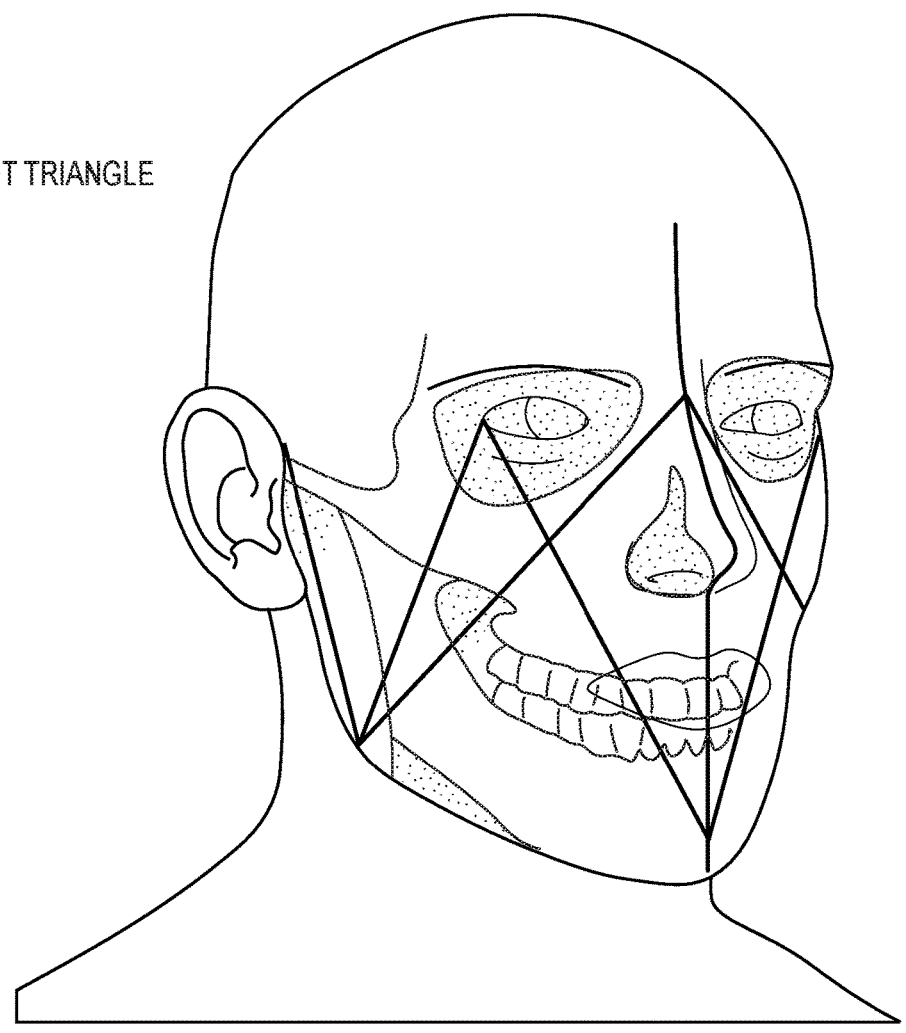

The following examples describe certain illustrative uses of the systems and methods described herein. Additional applications within reconstructive and/or plastic surgery include, but are not limited to, rhinoplasty, orthognatic and genioplasty, facial rejuvenation, facial reconstruction, ear reconstruction, fat grafting, head and neck microsurgery, and cleft lip/palate. FIGS. 3-5 show various views of measurements and analysis of a patient undergoing rhinoplasty.

Models (e.g., baseline model, simulation model, virtual models), guides and templates (e.g., custom guides/templates for marking progress during surgery) according to embodiments of the invention can be created for a patient completely based on their own anatomical data, and formed using additive manufacturing technologies including, but not limited to, color-jet 3D printing, selective laser sintering printing, and stereolithography printing.

A surgeon may use the baseline model and simulation model (representing an intended outcome) for visual reference, for example, during pre-operative and intra-operative planning for accurate measurements, planning for incision marks or suturing, planning for augmentation or reduction, understanding anatomical volume changes, etc. The custom guides and templates are physical manifestations of the changes, and can eliminate the guesswork for the surgeon on each case.

Periorbital Reconstruction

Figure 6:
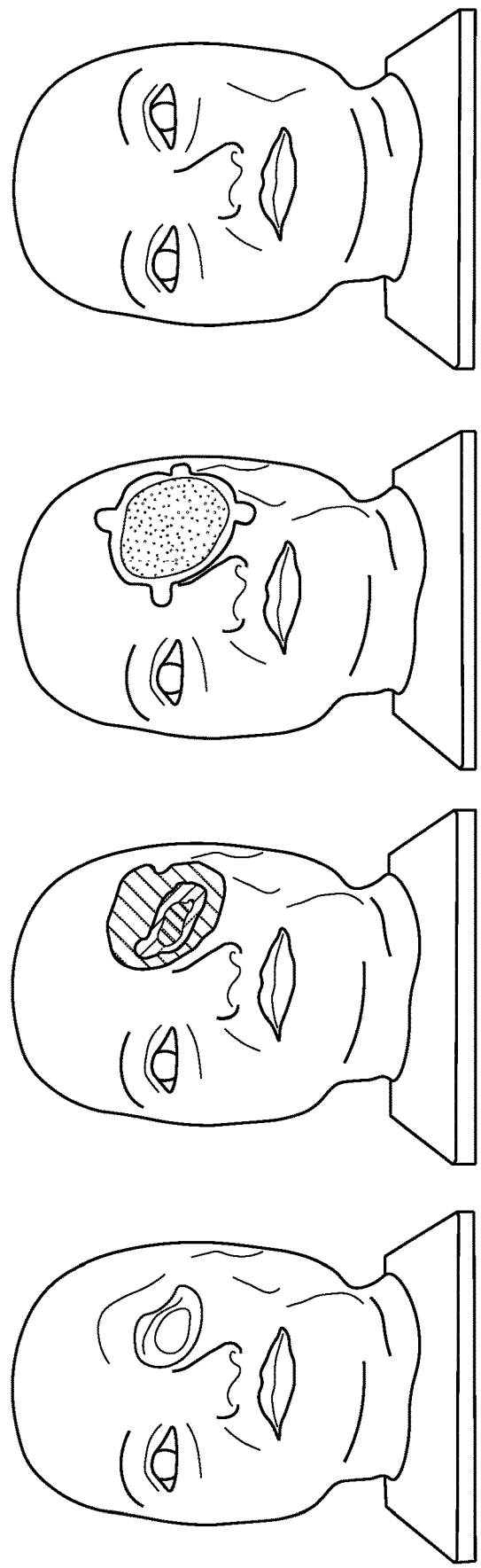
FIG. 6 shows illustrative 3D models and guides for periorbital reconstruction.

Soft tissue models and sterile guides were created to guide the plastic surgeon with fat injections for a periorbital reconstruction (see FIG. 6). 3D soft tissue data was used to create a baseline model and a simulated post-operative model. The normal side of the face was mirrored to the disfigured side of the face to create the simulated post-operative model so that the surgeon had the most accurate representation possible of the anatomical form. Two guides were created using the soft tissue models: an injection marking template (depicting topographic map and facial asymmetry); and an injection guide used to measure and document volumetric changes from serial injections. The marking template is for annotating on the patient the volumetric changes needed on the disfigured side of the face in order for the plastic surgeon to achieve facial symmetry. The injection guide serves as the end point of injection informing the plastic surgeon that the correct augmentation/symmetry has been reached. Without these guides, surgeons guess based on 2D photos or no references at all.

Dorsal Hump Reduction

Figure 7:
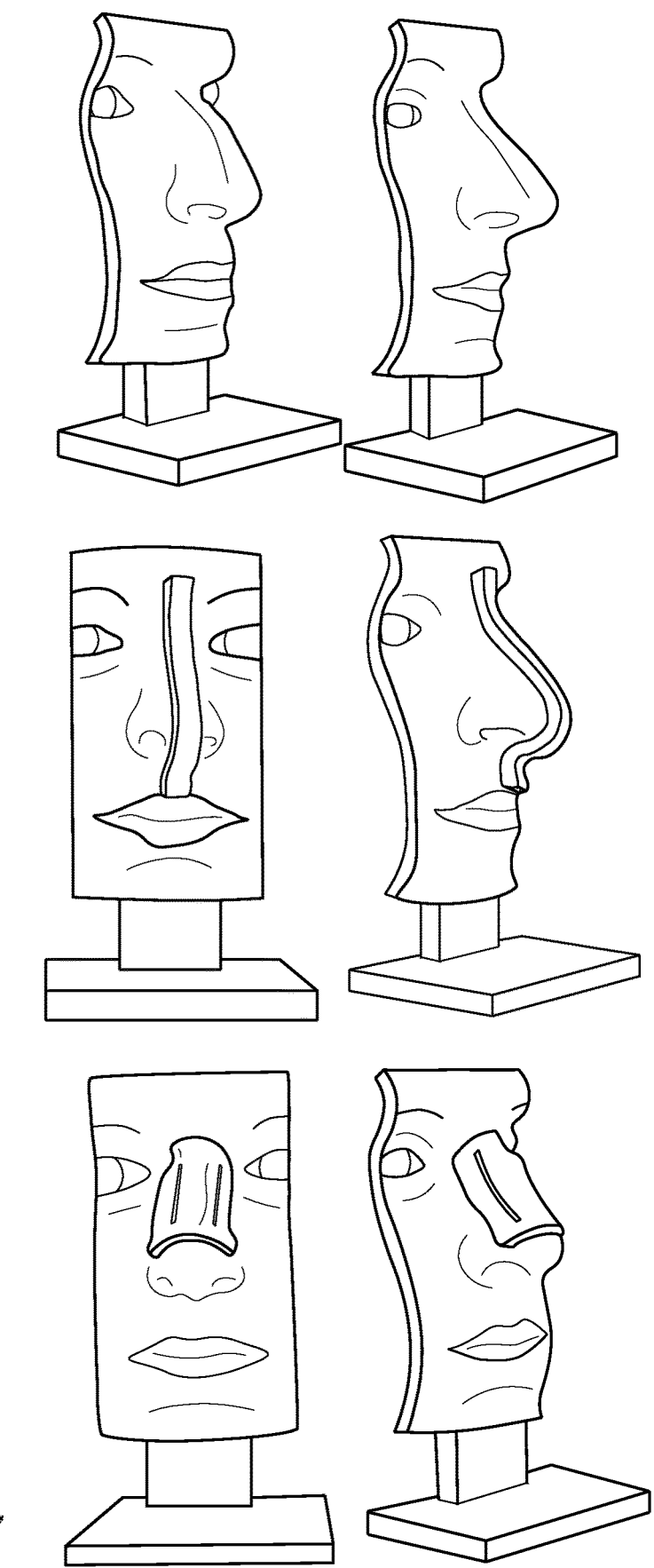
FIG. 7 shows illustrative 3D models and guides for dorsal hump reduction.

To complete a dorsal hump reduction, the plastic surgeon used 3D-printed models and guides (see FIG. 7) to eliminate guesswork and to fully understand the form of the patient for pre-operative and simulated post-operative conditions. Sterile guides were created based on the patient's pre-operative and simulated post-operative anatomical form. One guide accurately marked the dorsal hump reduction on each side of the nose, while another guide tracked the surgeon's process toward the simulated profile.

Forehead Flap Planning

Figure 8:
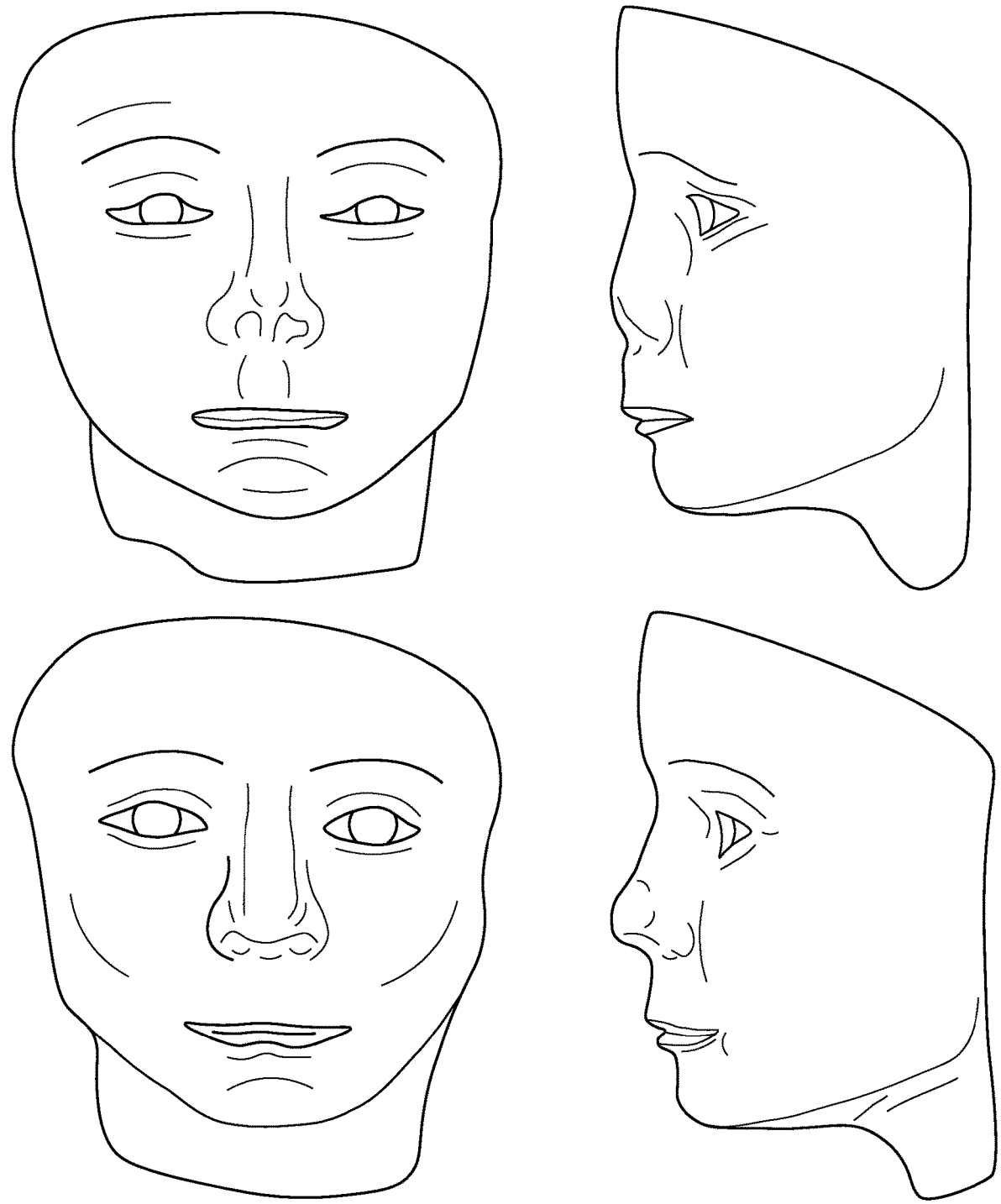
FIG. 8 shows illustrative 3D models for forehead flap planning.

A simulated model of a new nose was provided to assist a plastic surgeon with reconstructing the nose of a 7 year old (see FIG. 8). Using an age-matched control for the new nose, the plastic surgeon relied on the 3D model for planning the scaffolding and as a reference during the procedure.

While there have been shown and described fundamental novel features of the invention as applied to the preferred and exemplary embodiments thereof, it will be understood that omissions and substitutions and changes in the form and details of the disclosed invention may be made by those skilled in the art without departing from the spirit of the invention. Moreover, as is readily apparent, numerous modifications and changes may readily occur to those skilled in the art. For example, any feature(s) in one or more embodiments may be applicable and combined with one or more other embodiments. Hence, it is not desired to limit the invention to the exact construction and operation shown and described and, accordingly, all suitable modification equivalents may be resorted to falling within the scope of the invention as claimed. It is the intention, therefore, to be limited only as indicated by the scope of the claims appended hereto.

The invention claimed is:

1. A computer-implemented method of processing medical imaging data for use in reconstructive surgical procedures, comprising:
   receiving medical imaging data for a patient undergoing an aesthetic or reconstructive surgery, wherein the medical imaging data comprises a plurality of patient-specific 2D and/or 3D digital data sets from different 2D and/or 3D data sources;
   performing a vantage point centrality landmark identification procedure, locating and applying predetermined landmarks to each digital data set wherein each predetermined landmark represents proportional relationship data that provides alignment of the different 2D and/or 3D digital data sets; and
   performing an overlay analysis procedure; that aligns the plurality of 2D and/or 3D digital data sets from the different sources to create a unitary 3D digital representation of hard tissue, soft tissue and external anatomical imaging.

2. The computer-implemented method of claim 1, wherein the plurality of predetermined landmarks comprises at least five landmarks representing the right eye, left eye, nose, right mouth tip, and left mouth tip.

3. The computer-implemented method of claim 1, wherein the alignment is based on orbit and eye structure.

4. The computer-implemented method of claim 1, further comprising creating at least one of a baseline model, a simulated model, a template, and a guide based on the processed medical imaging data.

5. The computer-implemented method of claim 4, wherein the creating is performed using color jet 3D printing, selective laser sintering printing, or stereolithography printing.

6. The computer-implemented method of claim 1, further comprising providing one or more digital displays, comprising at least one of:
   a surgical planning display for pre-operative use, comprising a 2D and/or 3D display of the medical imaging data, the processed medical imaging data, or a simulated model based on the processed medical imaging data;
   a live data feed for intra-operative use, including an active data intake device updating in real time; and an automated data comparison display for post-operative use, configured to compare pre-operative and post-operative conditions.

7. The computer-implemented method of claim 6, wherein the active data intake device comprises an infrared scanner or depth sensing technology.

8. The computer-implemented method of claim 6, wherein at least one digital display comprises a virtual reality, augmented reality, or mixed reality device.

9. A patient-specific 3D model for use in reconstructive surgeries, produced by: receiving medical imaging data for a patient undergoing an aesthetic or reconstructive surgery, wherein the medical imaging data comprises a plurality of patient specific 2D and/or 3D digital data sets from different 2D and/or 3D data sources:
   processing the medical imaging data by:
   performing a vantage point centrality landmark identification procedure, locating and applying predetermined landmarks to each digital data set wherein each predetermined landmark is representative of proportional relationship data that provides alignment of the different digital data sets; and
   performing an overlay analysis procedure that aligns the plurality of 2D and/or 3D digital data sets from the different sources-to create a unitary 3D model based on the processed hard tissue, soft tissue and external anatomical medical imaging data.

10. The 3D model of claim 9, wherein the model is created using additive manufacturing technology.

11. The 3D model of claim 10, wherein the model is created using color-jet 3D printing, selective laser sintering printing, or stereolithography printing.

12. The 3D model of claim 10, wherein the model comprises at least one of a baseline model, a simulated model, a template, and a guide.

* * * * *